(12) United States Patent
Takai

(10) Patent No.: US 7,264,353 B2
(45) Date of Patent: Sep. 4, 2007

(54) OPHTHALMOLOGIC IMAGE-TAKING APPARATUS

(75) Inventor: Motoya Takai, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 510 days.

(21) Appl. No.: 10/487,994

(22) PCT Filed: Sep. 11, 2002

(86) PCT No.: PCT/JP02/09254

§ 371 (c)(1),
(2), (4) Date: Feb. 27, 2004

(87) PCT Pub. No.: WO03/026499

PCT Pub. Date: Apr. 3, 2003

(65) Prior Publication Data
US 2004/0239877 A1    Dec. 2, 2004

(30) Foreign Application Priority Data
Sep. 19, 2001    (JP)    ............................. 2001-285022

(51) Int. Cl.
*A61B 3/14*    (2006.01)
(52) U.S. Cl. ...................... 351/206; 351/208; 351/209; 351/211
(58) Field of Classification Search ................ 351/211, 351/246, 205, 208, 245, 237, 239, 209, 206, 351/204; 348/240
See application file for complete search history.

(56) References Cited

U.S. PATENT DOCUMENTS

| | | | |
|---|---|---|---|
| 4,370,033 A * | 1/1983 | Kani et al. ................... 351/206 |
| 4,699,481 A * | 10/1987 | Matsumura ................... 351/206 |
| 5,237,351 A | 8/1993 | Kohayakawa et al. ...... 351/243 |
| 5,572,266 A * | 11/1996 | Ohtsuka ....................... 396/18 |
| 5,701,157 A * | 12/1997 | Kato et al. ............. 348/240.99 |
| 5,757,461 A * | 5/1998 | Kasahara et al. ........... 351/206 |
| 5,894,337 A * | 4/1999 | Okinishi et al. ............ 351/205 |
| 6,158,864 A | 12/2000 | Masuda et al. ............. 351/206 |
| 6,327,375 B1 | 12/2001 | Matsumoto et al. ........ 382/117 |

FOREIGN PATENT DOCUMENTS

| | | |
|---|---|---|
| JP | 5-54777 | 8/1993 |
| JP | 7-284477 | 10/1995 |
| JP | 8-252224 | 10/1996 |
| JP | 11-313800 | 11/1999 |
| JP | 2000-296108 | 10/2000 |

* cited by examiner

*Primary Examiner*—Ricky Mack
*Assistant Examiner*—Tuyen Tra
(74) *Attorney, Agent, or Firm*—Fitzpatrick, Cella, Harper & Scinto

(57) ABSTRACT

A fixed target position which is synthesized and outputted is shifted to a correct position of a display device in accordance with an image pickup magnification of an eye to be examined. A state in which the imaging lens is moved to change an imaging magnification of an eye fundus image Pr of an eye to be examined E is indicated. If an image is magnified, the state wherein a mark M1 and a substantial center of a macular portion Po of the eye to be examined coincide with each other may change to the state wherein the macular portion Po is deviated from the mark M1. In such case, with respect to a shifting distance of the mark M1 required at this time, in the case where the position of the mark M1 is located at a distance of "a" from a center, when an image pickup magnification is n times, it is n·a from the center.

10 Claims, 6 Drawing Sheets

US 7,264,353 B2

OPHTHALMOLOGIC IMAGE-TAKING APPARATUS

TECHNICAL FIELD

The present invention relates to an ophthalmologic image-taking apparatus used in an ophthalmologic office, a group examination, or the like.

BACKGROUND ART

Up to now, an eye fundus camera in which a light source for leading an eye to be examined to a predetermined image-taking region is provided and the eye to be examined is fixed to the light source to image-take the predetermined region of the eye to be examined has been known from, for example, Japanese Patent Application Laid-Open No. 8-252224.

FIG. 7 shows a structure of a conventional eye fundus camera. On an optical path after an objective lens 1 which is opposite to an eye to be examined E, a perforated mirror 2 having an aperture provided at the center thereof, a focusing lens 3, an image-taking lens 4, a swing mirror 5 which is swingable, a field lens 9, a field stop 10, an imaging lens 11, and an image pickup element 12 are disposed. In a reflecting direction of the swing mirror 5, a relay lens 6, a liquid crystal plate 7 in which lighting is possible at an arbitrary position to fix the eye to be examined E, and a light source 8 are disposed for a fixation optical system.

Also, on an optical path in an incident direction of the perforated mirror 2, a lens 13, a ring stop 14, and a light source 15 are disposed. Note that the ring stop 14 is disposed to be substantially conjugate to the perforated mirror 2 with respect to the lens 13. An output of the image pickup element 12 is connected with a control circuit 16. A television monitor 17, an image-taking switch 18, and a fixed index shifting switch 19 are connected with the control circuit 16. Here, a region 17a of the television monitor 17 is within a substantial field of the eye to be examined E.

In order to image-take a predetermined region of the eye to be examined E, an operator lights a predetermined position of the liquid crystal plate 7. At this time, positional information of the liquid crystal plate 7 is converted into an electrical signal, and a mark M1 is generated in a position obtained according to the information and synthesized on an observation screen of the television monitor 17 as shown in FIG. 8, so that it is viewed by the operator. In addition, in the case where the predetermined region is changed, the fixed index shifting switch 19 such as a cross key is used, for example, thereby shifting a lighting position of the liquid crystal plate 7. At this time, the mark M1 located on the observation screen is also shifted on the screen in conjunction with a shift of the lighting position of the liquid crystal plate 7.

However, according to the above conventional example, when an image pickup magnification of the eye to be examined E is changed, a size of an image to be examined is changed on a display device. Here, the fixed target position which is synthesized and outputted to the display device are not changed either before or after changing the magnification, so that the macular portion of the eye to be examined E and the fixed target position are deviated from each other. With this state, when the eye to be examined E is led again, there is a problem in that the operator is hard to lead it because the macular portion and the fixed target position are deviated from each other.

Also, when an image of the eye to be examined is magnified to center a papillary portion on the screen, there is also a problem in that the operator is hard to determine the direction in which a fixation lead to the eye to be examined E is conducted because the macular portion is located outside a display area on the display screen.

DISCLOSURE OF THE INVENTION

An object of the present invention is to solve the above problems and to provide an ophthalmologic image-taking apparatus capable of shifting a fixed target position which is synthesized and outputted to a display device to a correct position in accordance with an image pickup magnification of an eye to be examined.

In order to achieve the above object, according to the present invention, an ophthalmologic image-taking apparatus is characterized by including: image pickup means for picking up an eye to be examined by a variable magnification; fixed index presenting means for presenting a fixed index to the eye to be examined at an arbitrary position; display means for synthesizing an image of the eye to be examined which is picked up by the image pickup means and a mark representing a fixed target position by the fixed index presenting means and displaying it; and control means for correcting a display position of the mark on the display means or an presenting position of the fixed index by the fixed index presenting means in accordance with the magnification of the image pickup means.

According to the present invention, there is provided an ophthalmologic image-taking apparatus as described above, in which the fixed index presenting means is a liquid crystal plate preferably.

According to the present invention, there is provided an ophthalmologic image-taking apparatus as described above, in which the fixed index presenting means is a light source in which a plurality of LEDs are arranged preferably.

According to the present invention, there is provided an ophthalmologic image-taking apparatus as described above, in which the image pickup means preferably picks up an eye fundus image of the eye to be examined, including a macular portion.

According to the present invention, there is provided an ophthalmologic image-taking apparatus as described above preferably further including a detector for detecting the magnification of the image pickup means.

According to the present invention, an ophthalmologic image-taking apparatus includes: image pickup means for picking up an eye to be examined by a variable magnification; fixed index presenting means for presenting a fixed index to the eye to be examined at an arbitrary position; display means for synthesizing an image of the eye to be examined which is picked up by the image pickup means and a mark representing a fixed target position by the fixed index presenting means and displaying it; and control means for causing the display means to display a mark representing a direction in which a macular portion is present when the macular portion of the eye to be examined cannot be displayed on the display means by increasing the magnification of the image pickup means.

BEST MODE FOR CARRYING OUT THE INVENTION

The present invention will be described in detail based on an embodiment of the present invention shown in FIGS. 1 to 6.

Figure 1:
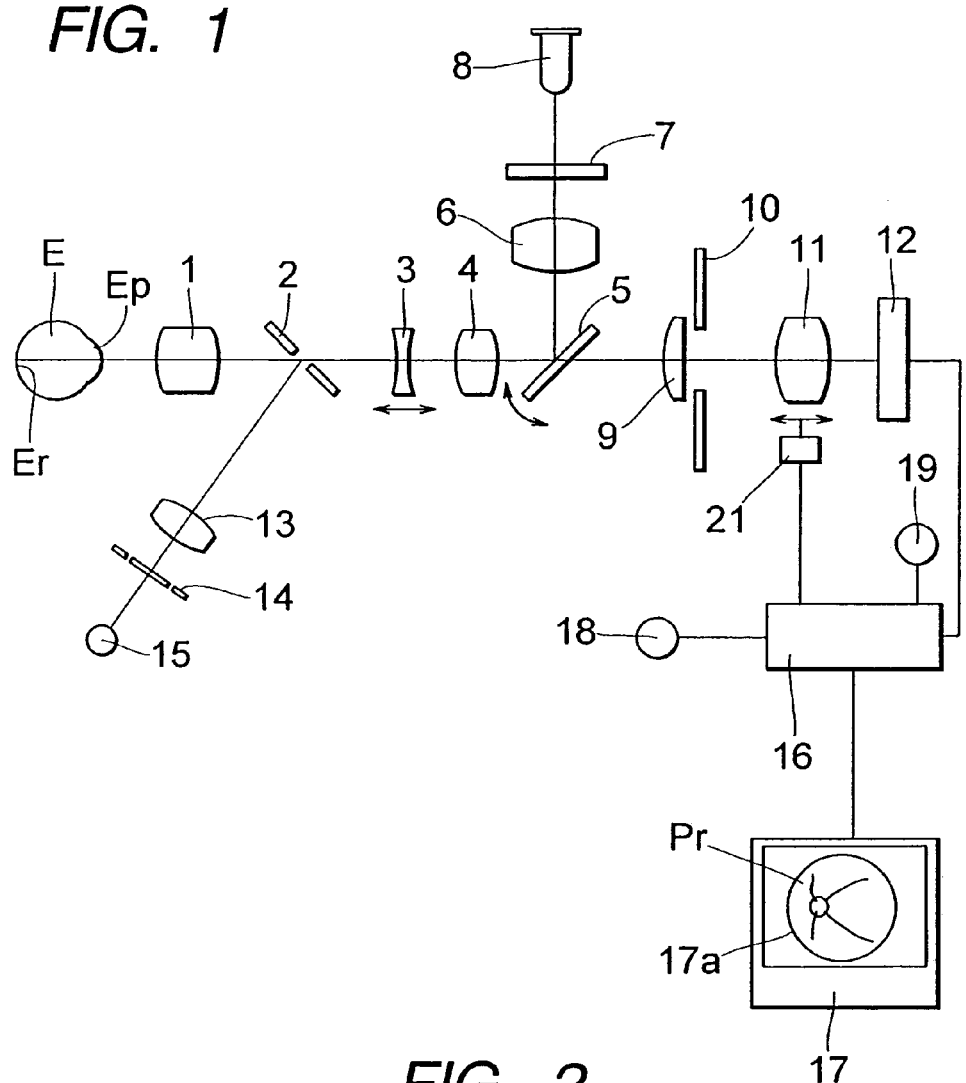
FIG. 1 shows a structure of an ophthalmologic image-taking apparatus according to an embodiment of the present invention.
Figure 7:
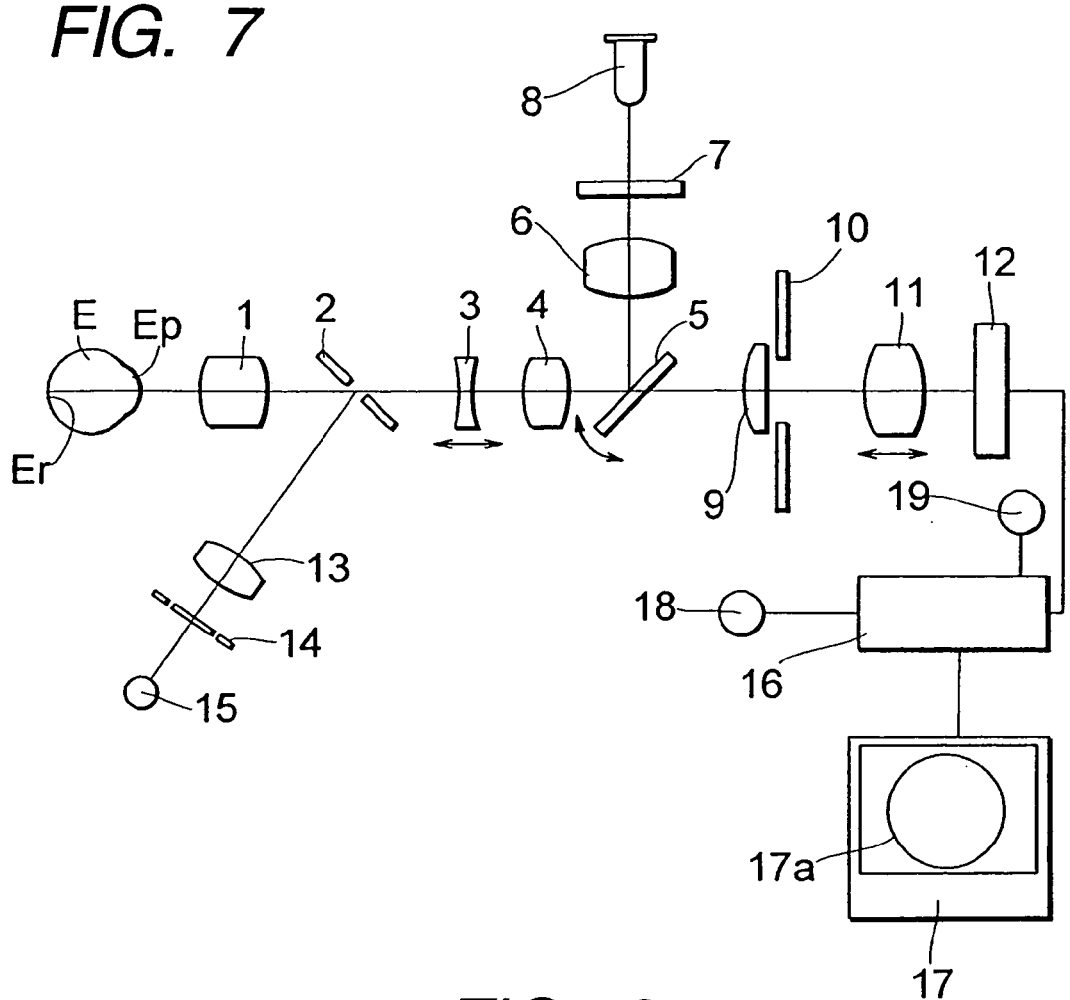
FIG. 7 is a side view of an ophthalmologic image-taking apparatus according to a conventional example.

FIG. 1 shows a structure of the embodiment. The same reference symbols as in FIG. 7 related to the conventional example indicate the same members. A detector 21 for detecting the position of an imaging lens 11 is provided and an output of the detector 21 is connected with a control circuit 16.

A light flux emitted from a light source 15 is passed through an aperture of a ring stop 14 and a lens 13, reflected toward the left by a mirror portion of a perforated mirror 2, and passed through an objective lens 1 to illuminate an eye fundus Er of an eye to be examined E. A reflected light flux from the eye fundus Er is passed through a pupil Ep, the objective lens 1, the aperture of the perforated mirror 2, a focusing lens 3, an image-taking lens 4, and a field lens 9, temporally imaged as an eye fundus image in the vicinity of a field stop 10, and imaged again in an image-taking element 12 by an imaging lens 11. An eye fundus image Pr imaged in the image-taking element 12 is converted into a video signal and displayed on a television monitor 17 through a control circuit 16.

Figure 2:
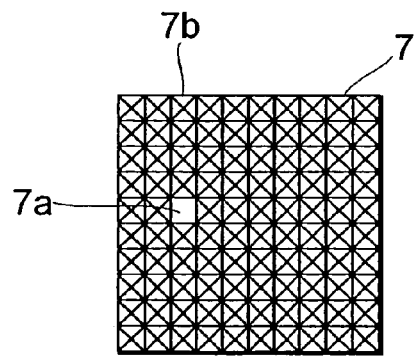
FIG. 2 is a front view of a fixed target.
Figure 8:
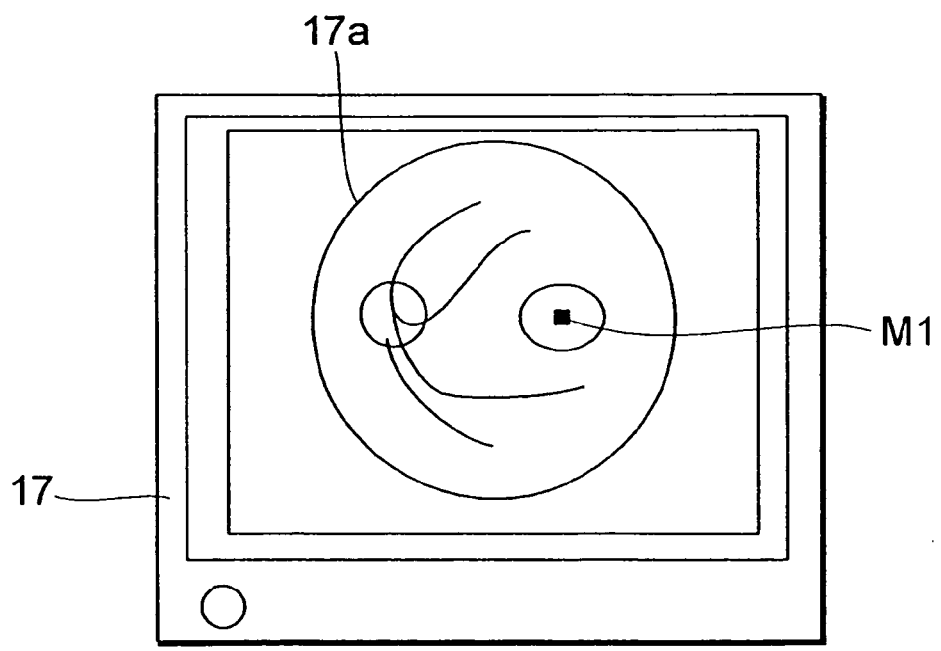
FIG. 8 is an explanatory view of an observation screen of the eye to be examined according to the conventional example.

An operator observes an eye fundus moving image displayed on the television monitor 17, adjusts the focusing lens 3 to focus the eye fundus image Pr, and operates a fixed index shifting switch 19 to image-take a predetermined region of the eye to be examined E. A state at this time is the same as in a television monitor screen shown in FIG. 8. The eye to be examined E is led to the predetermined region, and then an image-taking switch 18 is pushed on to emit light from the light source 15, and the eye fundus image Pr is stored as a still image in storage means provided within the control circuit 16. At this time, a positional relationship between an opening portion 7a of a liquid crystal plate 7 which becomes a fixed index and a light shielding portion 7b thereof is shown in FIG. 2.

Figure 3A:
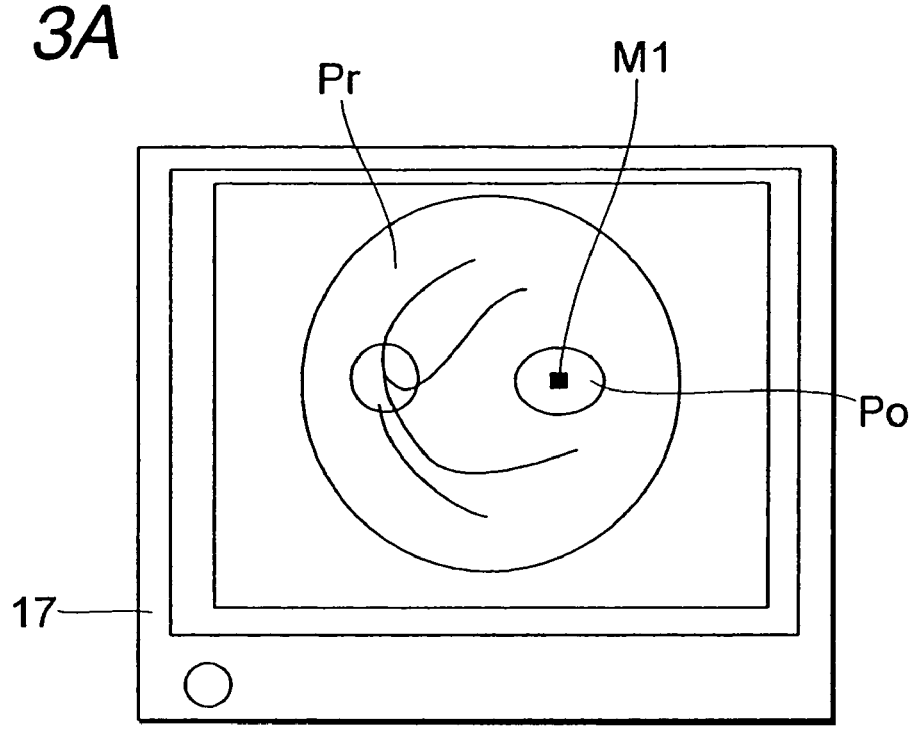
FIGS. 3A and 3B are explanatory views of an observation screen of an eye to be examined.
Figure 3B:
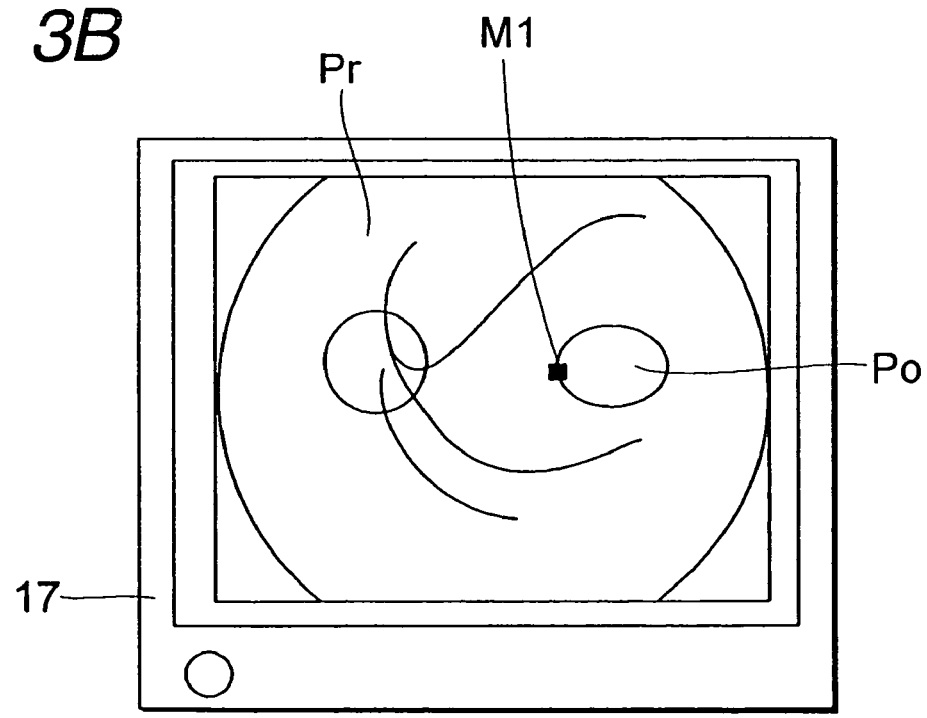

FIGS. 3A and 3B show a state in which the imaging lens 11 in FIG. 1 is moved in a direction indicated by an arrow to change an imaging magnification of the eye fundus image Pr of the eye to be examined E. When an image is magnified from FIG. 3A and FIG. 3B, in the case of FIG. 3A, a mark M1 and a substantial center of a macular portion Po of the eye to be examined coincide with each other. However, in the case of FIG. 3B, the macular portion Po is deviated from the mark M1.

Figure 4:
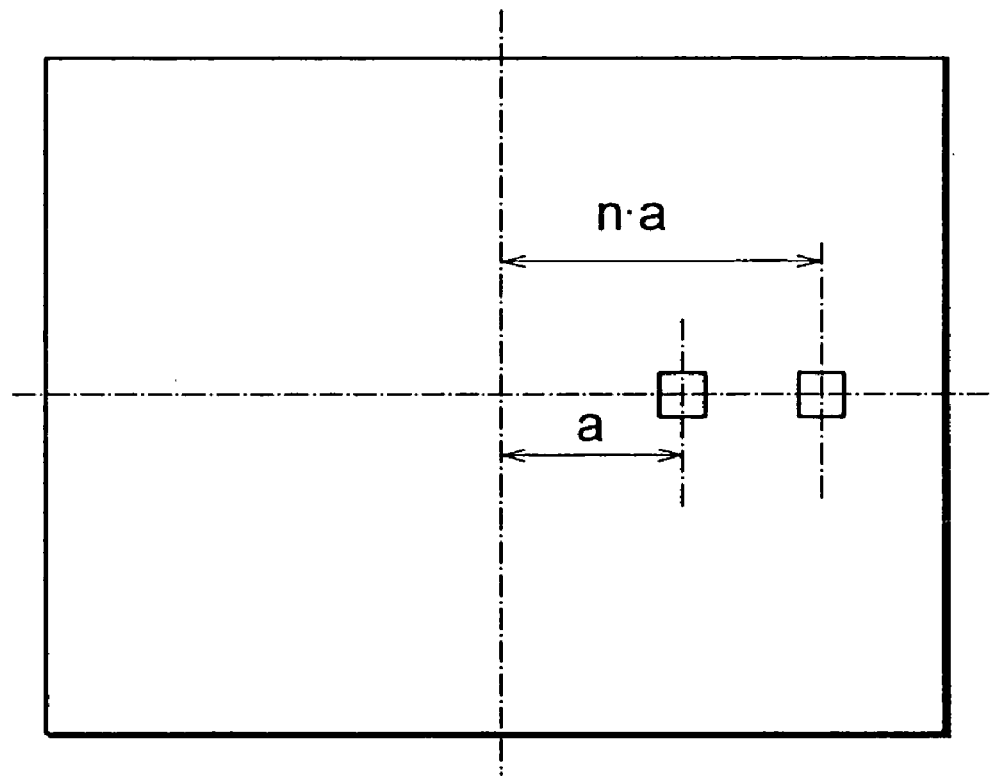
FIG. 4 is an explanatory view of the fixed target on the observation screen.

FIG. 4 shows a shifting distance of the mark M1 required at this time. In the case where the position of the mark M1 in FIG. 3A is located at a distance of "a" from a center, when an image pickup magnification is n times, it is preferably shifted to a position distanced by n·a from the center as shown in FIG. 4.

Figure 5:
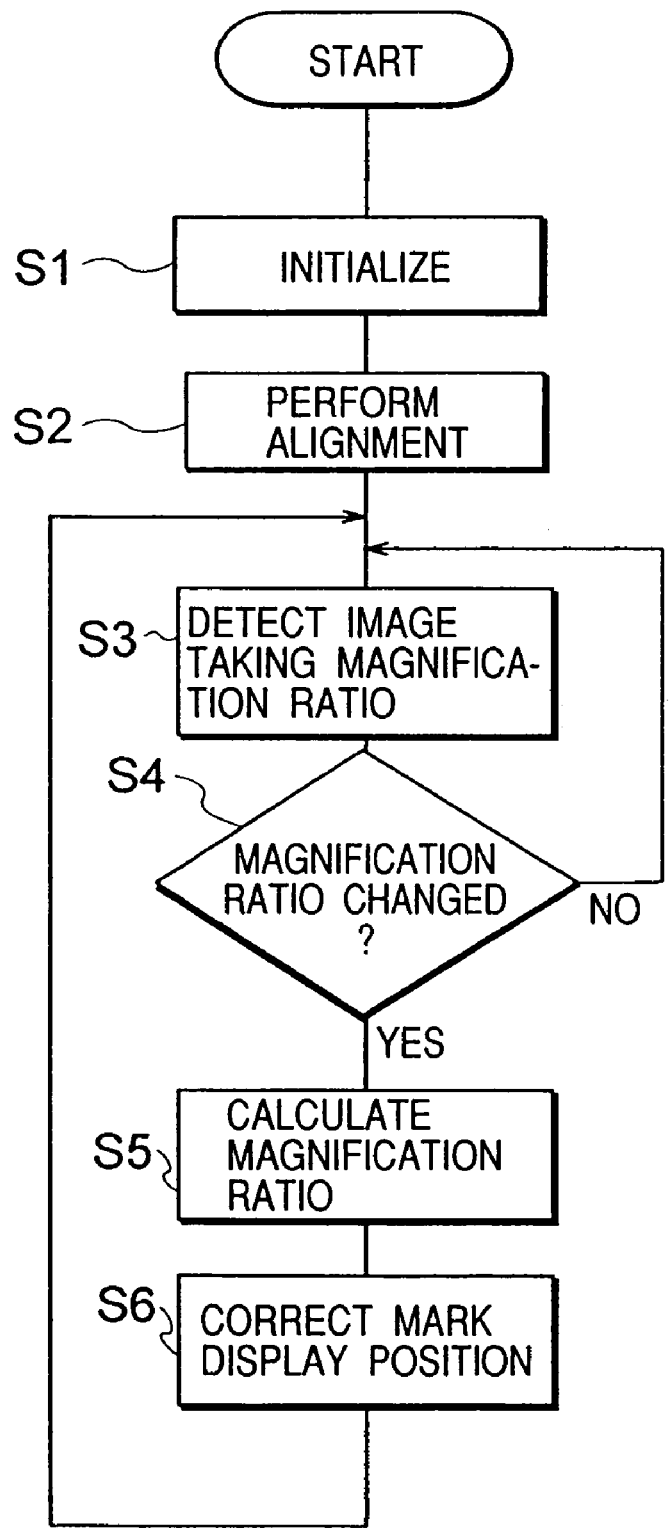
FIG. 5 is a flow chart of the operation performed in the embodiment of the present invention.

FIG. 5 is a flow chart showing a series of these operations. An initial condition is read in Step S1, and an alignment of the eye to be examined E is conducted in Step S2. In Step S3, a moving distance of the imaging lens 11 is detected by the detector 21, thereby detecting the image pickup magnification. In Step S4, whether or not the image pickup magnification is changed as compared with a previous image pickup magnification is determined. If it is changed, a magnification is calculated in Step S5. In Step S6, a mark display position is corrected such that the mark M1 is shifted by only a shifting distance according to the magnification.

Even in the case of fixation lead after the magnification is changed, it is preferable that the mark M1 is shifted in consideration of the magnification. In addition, in this embodiment, a change of magnification is conducted by moving the imaging lens 11 in an optical axis direction. However, it can be conducted according to insertion and removal of the imaging lens 11.

As a modified example, in the case of FIG. 3B, the macular portion Po of the eye to be examined is led to the position of the mark M1, and a pixel corresponding to the opening portion 7a of the liquid crystal plate 7 is changed such that the centers of both coincide with each other on the television monitor 17. Thus, the fixed index can be shifted.

Figure 6:
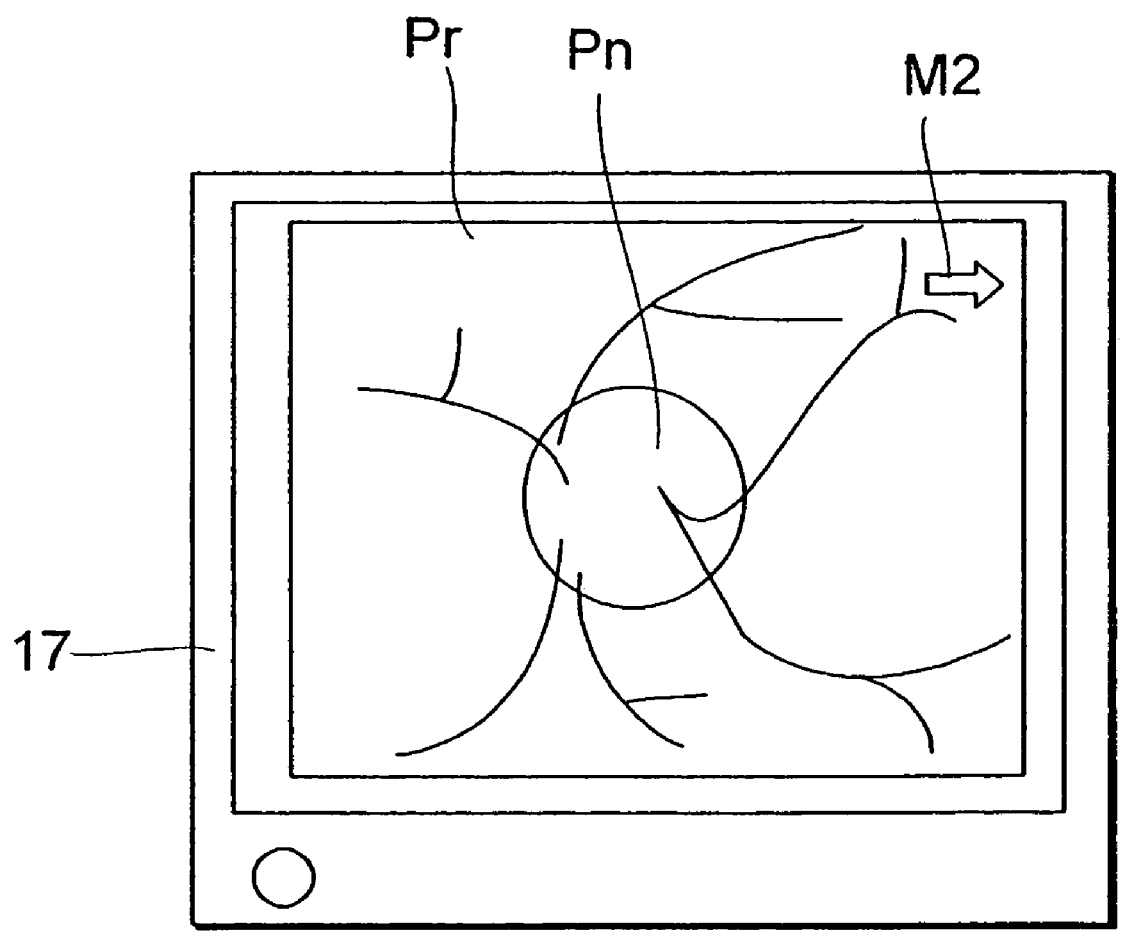
FIG. 6 is an explanatory view of the observation screen of the eye to be examined.

When macrophotography is conducted for a papillary portion Pn and the like of the eye fundus image Pr, the macular portion Po of the eye to be examined E is located outside a display area on the display screen. Thus, it is difficult to determine the position at which the macular portion Po is present at first sight. Therefore, as shown in FIG. 6, a mark M2 representing a direction is displayed, thereby indicating a direction in which the macular portion Po is present.

According to this embodiment, the mark M2 is displayed by using an arrow. However, display notifying an operator may be conducted by using character information such as "R and L", or it can be displayed by, for example, optically synthesizing an index instead of using an electrically synthesized image.

As described above, according to the ophthalmologic image-taking apparatus of the present invention, the image of the eye to be examined and the fixed target position which are synthesized and displayed can coincide with each other in accordance with the image pickup magnification of the eye to be examined. Thus, image-taking in which the eye to be examined is easy to lead can be efficiently conducted.

Also, even in an image-taking image which is obtained by macrophotography and has no macular portion, a direction of the macular portion can be indicated. Thus, a shift in a fixation lead is minimized and ophthalmologic image-taking can be efficiently executed.

The invention claimed is:

1. An ophthalmologic image-taking apparatus comprising:
    image pickup means for picking up an eye to be examined by a variable magnification;
    fixed index presenting means for presenting a fixed index to the eye to be examined at an arbitrary position;
    generating means for generating a mark corresponding to a position of the fixed index;
    display means for electronically synthesizing an image of the eye to be examined which is picked up by the image pickup means and the mark representing a fixed index position; and control means for correcting a display position of the mark on the display means in accordance with the magnification of the image pickup means.

2. An ophthalmologic image-taking apparatus according to claim 1, wherein the fixed index presenting means is a liquid crystal plate.

3. An ophthalmologic image-taking apparatus according to claim 1, wherein the fixed index presenting means is a light source in which a plurality of LEDs are arranged.

4. An ophthalmologic image-taking apparatus according to claim 3, wherein the image pickup means picks up an eye fundus image of the eye to be examined, including a macular portion.

5. An ophthalmologic image-taking apparatus according to claim 4, comprising a detector for detecting the magnification of the image pickup means.

6. An ophthalmologic image-taking apparatus according to claim 3, comprising a detector for detecting the magnification of the image pickup means.

7. An ophthalmologic image-taking apparatus according to claim 1, wherein the image pickup means picks up an eye fundus image of the eye to be examined, including a macular portion.

8. An ophthalmologic image-taking apparatus according to claim 7, comprising a detector for detecting the magnification of the image pickup means.

9. An ophthalmologic image-taking apparatus according to claim 1, comprising a detector for detecting the magnification of the image pickup means.

10. An ophthalmologic image-taking apparatus comprising:

image pickup means for picking up an eye to be examined by a variable magnification;

fixed index presenting means for presenting a fixed index to the eye to be examined at an arbitrary position;

display means for synthesizing an image of the eye to be examined which is picked up by the image pickup means and a mark representing a fixed index position: and control means for causing the display means to display a mark indicating a direction in which a macular portion of the eye to be examined is located when the macular portion is not displayed on the display means upon an increase in the magnification of the image pickup means.

* * * * *

UNITED STATES PATENT AND TRADEMARK OFFICE
CERTIFICATE OF CORRECTION

| | |
|---|---|
| PATENT NO. | : 7,264,353 B2 |
| APPLICATION NO. | : 10/487994 |
| DATED | : September 4, 2007 |
| INVENTOR(S) | : Motoya Takai |

Page 1 of 1

It is certified that error appears in the above-identified patent and that said Letters Patent is hereby corrected as shown below:

COLUMN 1:
Line 65, "is hard" should read --has trouble--.
Line 66, "to lead" should read --leading--.

COLUMN 2:
Line 3, "is hard to determine" should read --has trouble determining--.
Line 27, "an" should read --a--.

Signed and Sealed this

Twentieth Day of May, 2008

JON W. DUDAS
*Director of the United States Patent and Trademark Office*